(12) United States Patent
Hung et al.

(10) Patent No.: US 9,962,342 B1
(45) Date of Patent: May 8, 2018

(54) PHARMACEUTICAL COMPOSITION CONTAINING GUAIFENESIN AND APPLICATION THEREOF

(71) Applicant: Sunny Pharmtech Inc., New Taipei (TW)

(72) Inventors: Hao-Hsiang Hung, New Taipei (TW); Chia-Ching Ting, New Taipei (TW)

(73) Assignee: SUNNY PHARMTECH INC., New Taipei (TW)

( * ) Notice: Subject to any disclaimer, the term of this patent is extended or adjusted under 35 U.S.C. 154(b) by 0 days. days.

(21) Appl. No.: 15/458,207

(22) Filed: Mar. 14, 2017

(51) Int. Cl.
  *A61K 31/09* (2006.01)
  *A61K 9/50* (2006.01)

(52) U.S. Cl.
  CPC .......... *A61K 31/09* (2013.01); *A61K 9/5015* (2013.01); *A61K 9/5026* (2013.01); *A61K 9/5047* (2013.01)

(58) Field of Classification Search
  None
  See application file for complete search history.

(56) References Cited

U.S. PATENT DOCUMENTS

| | | | | | |
|---|---|---|---|---|---|
| 4,711,782 | A | * | 12/1987 | Okada ............... | A61K 9/1647 264/4.6 |
| 6,099,859 | A | * | 8/2000 | Cheng ............... | A61K 9/0004 424/464 |
| 2004/0259955 | A1 | * | 12/2004 | Umehara .......... | A61K 31/135 514/649 |
| 2005/0095288 | A1 | * | 5/2005 | Honea ............... | A61K 9/209 424/464 |
| 2013/0149383 | A1 | * | 6/2013 | Berkland ........... | A61K 31/09 424/490 |

* cited by examiner

*Primary Examiner* — Carlos A Azpuru
*Assistant Examiner* — Casey S Hagopian
(74) *Attorney, Agent, or Firm* — WPAT, PC

(57) ABSTRACT

The present invention provides a pharmaceutical composition containing Guaifenesin. The invention pharmaceutical composition comprises a core containing Guaifenesin and a coating layer encapsulating the core containing Guaifenesin, and the coating layer comprises a plasticizer and a polymer, wherein the polymer is applied in the range of approximately 5 wt. % to 35 wt. % based on the total weight of the pharmaceutical composition. A method for controlled releasing an expectorant agent is also provided in the present invention.

14 Claims, 1 Drawing Sheet

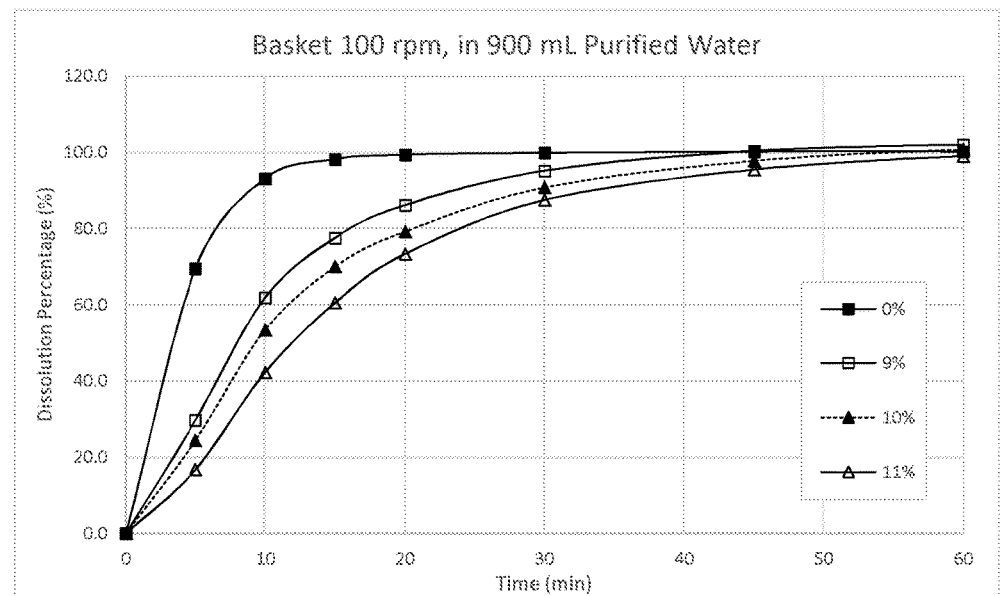

PHARMACEUTICAL COMPOSITION CONTAINING GUAIFENESIN AND APPLICATION THEREOF

TECHNICAL FIELD OF THE INVENTION

The present invention relates to a pharmaceutical composition containing Guaifenesin with the high potency taste masking while achieving total release of Guaifenesin in GI tract.

BACKGROUND OF THE INVENTION

Guaifenesin is an expectorant that increases the output of respiratory tract fluid. By reducing the viscosity of the secretions, guaifenesin increases the efficiency of the cough reflex and the ciliary action to remove accumulated secretions from trachea and bronchi. It is known to be readily absorbed form the intestinal tract and is rapidly metabolized (half-life of approximately 1 hour).

In previous bitter masking technique of guaifenesin granules, Carbopol or waxes were used as the control release materials. However, the potency of the granules is less than 50%.

Based on the aforementioned description, a high potency taste-masked pharmaceutical composition containing Guaifenesin for oral administration is required.

SUMMARY OF THE INVENTION

In one aspect, the present invention provides a pharmaceutical composition containing Guaifenesin. The invention pharmaceutical composition comprises a core containing Guaifenesin and a coating layer encapsulating the core containing Guaifenesin, and the coating layer comprises a plasticizer and a polymer, wherein the polymer is applied in the range of approximately 5 wt. % to 35 wt. % based on the total weight of the pharmaceutical composition.

In another aspect, the present invention discloses a method for controlled releasing an expectorant agent. The invention method comprises a step of administering a pharmaceutical composition containing an expectorant agent into oral, wherein the expectorant agent is characterized by not more than 30% release at the pH of the saliva in 5 mins but released over 75% in 45 mins.

In accordance with the present invention, the representative pharmaceutical composition containing Guaifenesin is the Guaifenesin bitter masked granule. The Guaifenesin bitter masked granule is microencapsulation, which is using the functional coating on the Guaifenesin powder or its crystals. The polymers comprises ethyl cellulose are used as the function coating material. By providing uniform, impervious high coating levels on bitter Guaifenesin powder or crystals, the present invention not only provides extremely effective taste masking, but the drug substance, Guaifenesin is controlled releasing and can dissolve over 75% in 45 minutes (the USP recommended dissolution method; basket 100 rpm, 900 mL purified water).

The taste-masked granules obtained as described aforementioned are optional blended with other pharmaceutically acceptable excipients such as flavors, sweeteners, and preservatives and filled into unit dose containers or compressed into effervescent, fast disintegrating or chewable tablets. The granules can also blend with other active ingredients to make the oral powder for cold symptoms relief. All the formulations are suitable for the pediatric and geriatric patients who are unwilling and/or find it difficult to swallow tablets. Especially the fast disintegrating tablets are commonly used since it is rapidly disintegrate in the mouth. Therefore, it would be suitable for oral administration to patients who is difficult to swallow tablets. The advantage of the invention is the Guaifenesin Bitter Masked granules are slowly dissolved in first 5 minutes, but it can still dissolve over 75% in 45 minutes.

BRIEF DESCRIPTION OF THE DRAWINGS

FIG. 1 illustrates the dissolution curve of the claimed pharmaceutical composition with 0 wt. %, 9 wt. %, 10 wt. % and 11 wt. % coating polymer, respectively. The dissolution method is USP apparatus 1, basket, 100 rpm in 900 mL purified water.

BRIEF DESCRIPTION OF THE PREFERRED EMBODIMENTS

In one embodiment, the present invention discloses a pharmaceutical composition containing Guaifenesin. The invention pharmaceutical composition comprises a core containing Guaifenesin and a coating layer encapsulating the core containing Guaifenesin, and the coating layer comprises a plasticizer and a polymer, wherein the polymer is applied in the range of approximately 5 wt. % to 35 wt. % based on the total weight of the pharmaceutical composition.

In one example of the embodiment, the Guaifenesin release not more than 50% in the initial 5 mins dissolution test at pHs of the saliva but it release at least 75% within approximately 45 mins at pHs of the upper intestinal tract.

In one example of the embodiment, the Guaifenesin release not more than 50% in the initial 5 mins of pHs of the saliva.

In one example of the embodiment, the core containing Guaifenesin further comprises a seal coated material that includes a shellac, a plasticized hydroxypropyl methylcellulose, an enteric methylmethacrylate copolymer and ethylcellulose.

In one example of the embodiment, the plasticizer comprises polyethylene glycol, dibutyl sebacate, diethylphthalate, phthalic acid derivatives, triacetin and citric acid esters.

In one example of the embodiment, the polymer comprises methacrylic ester copolymer, cellulose acetate phthalate, hydroxypropylmethyl cellulose phthalate, ethylcellulose and methacrylic acid-methylmethacrylate copolymers.

In one example of the embodiment, the polymer is applied in the range of approximately 5 wt. % to 35 wt. % based on the total weight of the pharmaceutical composition.

In one example of the embodiment, the optional seal coat is applied in the range up to 3 wt. % based on the total weight of the pharmaceutical composition.

In one example of the embodiment, the invention pharmaceutical composition is a taste masking drug formulation.

In one example of the embodiment, the pharmaceutical composition is one selected from the group consisting of powder, capsule, microcapsule, granule and tablet.

Typically, the present invention provides a taste-masked Guaifenesin granule is suitable for oral administration as a fast-disintegrating, chewable tablet, oral powder and more specifically relates to such oral dosage forms in which the bitter taste of Guaifenesin contained therein is masked by a microencapsulation by subsequent functional membrane coating on Guaifenesin crystal.

A taste-masked microcapsule composition for taste masking is an orally effective Guaifenesin in accordance with the guaifenesin crystal. The Guaifenesin crystal may be coated with an optional seal coat in advance and then coated with a plasticized enteric or an insoluble polymer. In the resulting composition of the taste-masked microcapsule, the coating polymer is applied in the range of approximately 5 wt. % to 35 wt. % based on the total weight of the pharmaceutical composition. The taste-masked granules thus obtained release less than 50%, most preferably less than 30%, at a pH of 4.0 to 6.0 (pH of the saliva) in first 5 minutes, but it can release over 75% in 45 minutes. Therefore, the bitter taste of Guaifenesin is decreased, and it can still be absorbed in the gastrointestinal (GI) tract during the orally administered.

In general, these Guaifenesin powders or crystals are coated with an enteric or insoluble polymer coat. Enteric polymers suitable for functional coating include methacrylic ester copolymer, cellulose acetate phthalate and hydroxypropylmethyl cellulose phthalate. Insoluble polymers suitable for functional coating include ethylcellulose. Particularly preferred enteric polymers are methacrylic acid-methylmethacrylate copolymers. These polymers can be plasticized using conventional plasticizers in an amount of about 5 wt. % to 30 wt. % based on the weight of the entire and insoluble polymer. Representative examples of plasticizers are polyethylene glycol, dibutyl sebacate, diethylphthalate, phthalic acid derivatives, triacetin and citric acid esters (acetyl tributyl citrate, triethyl citrate). Both aqueous and solvent based functional coating materials can be used.

The coating polymers are applied in the range of approximately 5 wt. % to 35 wt % based on the total weight of the pharmaceutical composition. In this product, guaifenesin bitter masking granule, the enteric polymer typically is 10 to 35 wt. %, preferably 20 to 30. wt. %, the insoluble polymer typically is 5 to 30 wt %, preferably 10 to 20 wt %, and the optional seal coat is applied in the range up to 3 wt. % based on the total weight of the pharmaceutical composition.

In general coating process, a drying step should preferably be carried out for such a time period and at such temperatures so as to reduce residual solvent level below the recommended for human consumption after application of the ethylcellulose. In this manufacture process, the purified water is the major dispersion solution. Therefore, the main property of drying step is to shape the bitter masking particle and decrease the water amount of the granule.

The material of choice for the seal coat is plasticized pharmaceutical grade shellac. Other seal coat materials such as Colorcon Opadry, a plasticized hydroxypropylmethylcellulose (HPMC) formulation, can be used for the same purpose.

Both enteric and insoluble polymer coatings can be formed by spraying solutions in organic solvents or suspensions in purified water. The seal coat may also be applied as an outer coat. The polymeric coatings may contain certain pigments and opacifiers to promote compliance, product differentiation or purely for aesthetic reasons.

In one example of the embodiment, the mean particle size of the microcapsules will be in the range of about 100 to 1000 microns, most preferably in the range of about 150 to 800 microns.

In another embodiment, the present invention provides a method for controlled releasing an expectorant agent. The method comprises the step of administering a pharmaceutical composition containing an expectorant agent into oral, wherein the expectorant agent is characterized by not more than 30% release at the pH of the saliva in 5 mins but released over 75% in 45 mins.

In one example of the another embodiment, the expectorant agent is Guaifenesin.

In one example of the another embodiment, the pharmaceutical composition containing the expectorant agent comprises a core containing Guaifenesin and a coating layer encapsulating the core containing Guaifenesin, and the core containing Guaifenesin comprises a plasticizer and a polymer, wherein the polymer is applied in the range of approximately 5 wt. % to 35 wt. % based on the total weight of the pharmaceutical composition.

In one example of the another embodiment, the core containing Guaifenesin further comprising a seal coated material which includes a shellac, a plasticized hydroxypropyl methylcellulose, an enteric methylmethacrylate copolymer and ethylcellulose.

In one example of the another embodiment, the plasticizer comprises polyethylene glycol, dibutyl sebacate, diethylphthalate, phthalic acid derivatives, triacetin and citric acid esters.

In one example of the another embodiment, the polymer comprises methacrylic ester copolymer, cellulose acetate phthalate, hydroxypropylmethyl cellulose phthalate, ethylcellulose and methacrylic acid-methylmethacrylate copolymers.

In one example of the another embodiment, the polymer is applied in the range of approximately 5 wt. % to 35 wt. % based on the total weight of the pharmaceutical composition.

In one example of the another embodiment, the optional seal coat is applied in the range up to 3 wt. % based on the total weight of the pharmaceutical composition.

In one example of the another embodiment, the pharmaceutical composition containing an expectorant agent is one selected from the group consisting of powder, capsule, microcapsule, granule and tablet.

Mostly, the different lots of the invention pharmaceutical composition containing Guaifenesin have been found to release less than 50%, most preferably less than 30%, at a pH of 4.0 to 6.0 (pH of the saliva) in first 5 minutes, but it can release over 75% in 45 minutes.

Various types of formulations may be prepared using the taste masked Guaifenesin microcapsules disclosed in this invention, including powder dispersions, capsules filled with free-flowing particulate material, effervescent tablet, fast disintegrating tablet, and chewable tablet formulations. These solid formulations may contain about 10 weight % to 95 weight % microcapsules. Actual methods of preparing such dosage forms are well known to those skilled in this art. For these formulations, conventional carriers, sweeteners, flavoring/coloring additives and tableting aids will be employed, which include, but are not limited to, ingredients such as binders, disintegrants, wetting agents, dilleunts and lubricating agents. Binders include, but are not limited to, Klucel LF (hydroxypropylcellulose) and Avicel (microcrystalline cellulose). Disintegrants include, but are not limited to, cornstarch, lactose, mannitol, sucrose, Avicel (microcrystalline cellulos), Primogel (sodium carboxymethyl starch), Emcompress (dibasic calcium pholyvinyl pyrrolidone), and tricalcium phosphate. Wetting agents include, but are not limited to, sodium lauryl sulfate. Lubricating agents include, but are not limited to stearates (e.g. magnesium, calcium, and sodium), stearic acid, sterotex, talc, waxes and stearowet. Components will be incorporated in formulations, which promote effervescence, i.e., release of gas (carbon dioxide) upon contact with water; these components include a combination of a carbonate salt, such as sodium bicarbonate, and an organic acid such as citric acid.

In addition to the dosage forms listed earlier, the taste-masked microcapsules, due to their free flowing characteristics, may be used in the development of sustained/modified release tablet/capsule formulations. Additional objects, advantages and novel features of the invention will become apparent to those skilled in the art upon examination of the examples provided, or upon practicing the invention.

Example 1

Guaifenesin crystals are used in this manufacture process. These microcapsules are coated by fluid bed coating unit, Versa Glatt, with a suspension of Eudragit L30D. The coating amount of the Eudragit L30D polymer is 20 wt. % based on the total weight of the pharmaceutical composition, with triethyl citrate as the plasticizer. The taste masked granules thus have been found to release less than 50%, most preferably less than 30% during the initial 5 mins, at a pH of 4.0 to 6.0 respectively using USP Apparatus 1 (900 mL of pH 4.0 or pH 6.8 buffer, Basket, 50 rpm and 100 rpm, respectively).

Example 2

The Guaifenesin crystals is changed to obtain an ethylcellulose coating process. The coating amount of the ethylcellulose is 20 wt. % based on the total weight of the pharmaceutical composition. These microcapsules are first coated using Glatt GPCG 5 fluid bed coater with a optional seal coat of 3 wt. % shellac and further coated with a suspension of Eudragit L30D for 20 wt. %, with acetyl tributyl citrate as the plasticizer. The taste masked granules thus have been found to release less than 50%, most preferably less than 30% during the initial 5 mins, at a pH of 4.0 to 6.0 respectively using USP Apparatus 1 (900 mL of pH 4.0 or pH 6.8 buffer, Basket, 50 rpm and 100 rpm, respectively).

Example 3

The Guaifenesin crystals is changed to obtain an ethylcellulose coating, which the coating weight gain is 20 wt. % based on the pharmaceutical composition. These microcapsules are coated for 20 wt. % weight gain with a suspension of the 4:1 blend of Eudragit L30D and ethylcellulose (Aquacoat ECD-30 from FMC), with triethylcitrate and dibutyl sebacetae, respectively, as the plasticizer. The taste-masked granules have been observed to release in an hour not more than 10% at pH 4.0 and over 80% at pH 6.8.

Example 4

The Guaifenesin crystals is changed to obtain an ethylcellulose coating materials, which the coating weight gain is 20 wt. % based on the pharmaceutical composition. weight gain. These microcapsules are coated for 20 wt. % weight gain with a suspension of ethylcellulose (Aquacoat ECD-30 from FMC), with triethylcitrate, dibutyl sebacetae or triacetin, respectively, as the plasticizer. The taste masked granules thus have been found to release less than 50%, most preferably less than 30% during the initial 5 mins, at a pH of 4.0 to 6.0 buffer. These microcapsules are coated with a suspension of ethylcellulose (Aquacoat ECD-30 from FMC), with triethylcitrate, dibutyl sebacetae or triacetin, respectively, as the plasticizer. The coating amount of the ethylcellulose is 20 wt. % based on the pharmaceutical composition.

Example 5: Dissolution Experiment

The ingredients of test formulations for dissolution experiment are list in TABLE 1.

TABLE 1

| Ingredients | Wt. |
|---|---|
| Guaifenesin | 65.0-95.0 |
| Eudragit L30D + Aquacoat ECD Or Aquacoat ECD | 4.7-26.9 |
| Triacetin | 0.2-8.1 |
| Shellac | 0.0-3.0 |
| Purified Water | q.s. |
| Total Solid Weight | 100.0 |

General procedure is described as follows: Firstly, place 100.0-115.0 mg pharmaceutical composition into capsule. Secondly, place the capsule into 900 mL purified water with 100 rpm basket in 37° C. Thirdly, sampling at each time point. Fourthly, all the samples is scanned by 276 nm UV detector or HPLC. 'the experimental data is list in TABLE 2 and illustrated in FIG. 1. According to the TABLE 2, the Guaifenesin release not more than 50% in the initial 5 mins, but it release at least 75% within approximately 30 mins when the guaifenesin crystal coated with different weight gain polymer.

TABLE 2

| Time(min) | 0% | 9% | 10% | 11% |
|---|---|---|---|---|
| 0 | 0.0 | 0.0 | 0.0 | 0.0 |
| 5 | 69.5 | 29.7 | 24.4 | 16.7 |
| 10 | 93.1 | 61.9 | 53.4 | 42.2 |
| 15 | 98.2 | 77.6 | 70.0 | 60.6 |
| 20 | 99.4 | 86.1 | 79.2 | 73.3 |
| 30 | 99.9 | 95.1 | 90.7 | 87.4 |
| 45 | 100.2 | 100.3 | 97.7 | 95.4 |
| 60 | 100.2 | 102.0 | 100.7 | 99.0 |

While the invention has explained in relation to its preferred embodiments, it is well understand that various modifications thereof will become apparent to those skilled in the art upon reading the specification. Therefore, the invention disclosed herein intended to cover such modifications as fall within the scope of the appended claims.

What is claimed is:
1. A pharmaceutical composition, comprising:
   a core, consisting of guaifenesin crystals coated with a shellac; and
   a coating layer, encapsulating the core, the coating layer comprising:
      a plasticizer; and
      a polymer, wherein the polymer is applied in the range of approximately 5 wt. % to 35 wt. % based on the total weight of the pharmaceutical composition.
2. The pharmaceutical composition of claim 1, wherein the guaifenesin releases not more than 50% in the initial 5 mins dissolution test at pHs of the saliva but it releases at least 75% within approximately 45 mins at pHs of the upper intestinal tract.
3. The pharmaceutical composition of claim 2, wherein the guaifenesin release not more than 50% in the initial 5 mins of pHs of the saliva.
4. The pharmaceutical composition of claim 1, wherein the plasticizer comprises polyethylene glycol, dibutyl sebacate, diethylphthalate, phthalic acid derivatives, triacetin or citric acid esters.
5. The pharmaceutical composition of claim 1, wherein the polymer comprises methacrylic ester copolymer, cellu- lose acetate phthalate, hydroxypropylmethyl cellulose phthalate, ethylcellulose or methacrylic acid-methylmethacrylate copolymers.

6. The pharmaceutical composition of claim 1, wherein the shellac is applied in the range up to 3 wt. % based on the total weight of the pharmaceutical composition.

7. The pharmaceutical composition of claim 1, being a taste masking drug formulation.

8. The pharmaceutical composition of claim 1, being one selected from the group consisting of powder, capsule, microcapsule, granule and tablet.

9. The pharmaceutical composition of claim 8, wherein a mean particle size of the microcapsules is in the range of about 100 to 1000 microns.

10. A method for controlled releasing of an expectorant agent, comprising:
    orally administering a pharmaceutical composition comprising:
        a core, consisting of guaifenesin crystals coated with a shellac; and
        a coating layer, encapsulating the core, the coating layer comprising:
            a plasticizer; and
            a polymer, wherein the polymer is applied in the range of approximately 5 wt. % to 35 wt. % based on the total weight of the pharmaceutical composition;
    wherein the guaifenesin agent is characterized by not more than 30% release at the pH of the saliva in 5 mins but released over 75% in 45 mins.

11. The method of claim 10, wherein the plasticizer comprises polyethylene glycol, dibutyl sebacate, diethylphthalate, phthalic acid derivatives, triacetin or citric acid esters.

12. The method of claim 10, wherein the polymer comprises methacrylic ester copolymer, cellulose acetate phthalate, hydroxypropylmethyl cellulose phthalate, ethylcellulose or methacrylic acid-methylmethacrylate copolymers.

13. The method of claim 10, wherein the shellac is applied in the range up to 3 wt. % based on the total weight of the pharmaceutical composition.

14. The method claim 10, wherein the pharmaceutical composition is one selected from the group consisting of powder, capsule, microcapsule, granule and tablet.

* * * * *